United States Patent [19]

Schochetman et al.

[11] Patent Number: 5,037,750

[45] Date of Patent: Aug. 6, 1991

[54] METHOD FOR PRODUCING ANTIBODIES WHICH CATALYZE CHEMICAL REACTIONS

[75] Inventors: Gerald Schochetman; Richard J. Massey, both of Rockville, Md.

[73] Assignee: Igen, Inc., Rockville, Md.

[21] Appl. No.: 411,547

[22] Filed: Sep. 22, 1989

Related U.S. Application Data

[60] Division of Ser. No. 674,253, Nov. 27, 1984, Pat. No. 4,888,281, which is a continuation-in-part of Ser. No. 556,016, Nov. 29, 1983, abandoned.

[51] Int. Cl.$^5$ .................... C12N 9/00; C12N 15/02; A61K 39/395
[52] U.S. Cl. .................... 435/183; 435/193; 435/196; 435/172.2; 424/85.8; 530/387
[58] Field of Search ............ 435/183, 193, 196, 172.2; 424/85.8; 530/387, 388

[56] References Cited

U.S. PATENT DOCUMENTS 4,888,281 12/1989 Schochekman et al. ............. 435/72

Primary Examiner—Elizabeth C. Weimar
Assistant Examiner—Charles L. Patterson, Jr.
Attorney, Agent, or Firm—Barry Evans

[57] ABSTRACT

A method for increasing the rate of chemical reactions involving the conversion of at least one reactant to at least one product involves contacting the reactant with an appropriate monoclonal antibody under conditions permitting the formation of a complex between the antibody and the reactant. The complexed reactant is converted to the product which is then released from the complex. The monoclonal antibody may employ a cofactor and may be directed to a known substrate of an enzyme. Methods for preparing such monoclonal antibodies are also disclosed.

13 Claims, No Drawings

METHOD FOR PRODUCING ANTIBODIES WHICH CATALYZE CHEMICAL REACTIONS

This application is a division of application Ser. No. 674,253, now U.S. Pat. No. 4,888,281, filed Nov. 27, 1984, which is a continuation-in-part of application Ser. No. 556,016, filed Nov. 29, 1983, now abandoned.

The present invention relates to the use of monoclonal antibodies to catalyze chemical reactions. Monoclonal antibodies are immunoglobulins produced by hybridoma cells. A monoclonal antibody reacts with a single antigenic determinant and provides greater specificity than a conventional, serum-derived antibody. Furthermore, screening a large number of monoclonal antibodies makes it possible to select an individual antibody with desired specificity, avidity and isotype. Hybridoma cell lines provide a constant, inexpensive source of chemically identical antibodies and preparations of such antibodies can be easily standardized. Methods for producing monoclonal antibodies are well known to those of ordinary skill in the art, e.g., Koprowski, H. et al., U.S. Pat. No. 4,196,265, issued Apr. 1, 1980.

Antigen recognition by a monoclonal antibody is attributable to a specific combining site in the N-terminal region of the immunoglobulin (Ig) molecule. Ig molecules are thought to react with antigens via the same types of short range forces characteristic of all protein-protein interactions. Antigen-antibody interactions are highly specific because of the complementary three-dimensional shapes of the antibody's combining site and of the corresponding antigenic determinant or epitope. Such complementary shapes permit the molecules to approach each other closely and to interact over a substantial surface area. The specificity of antibody-antigen interactions is evidenced by the fact that changes in the configuration of the antigenic determinant result in marked decreases in the binding constant of the antigen to the antibody. The binding constant of an antibody for its antigen is generally much higher than that of an enzyme for its substrate.

Uses of monoclonal antibodies are known. One such use is in diagnostic methods, e.g., David, G. and Greene, H., U.S. Pat. No. 4,376,110, issued March 8, 1983.

Monoclonal antibodies have also been used to recover materials by immunoadsorption chromatography, e.g., Milstein, C., 1980, Scientific American 243:66, 70.

However, it has not been suggested that monoclonal antibodies can be used to catalyze chemical reactions. Indeed, the field of catalysis has developed independently from the field of immunology. The only reported attempt at using antibodies as catalysts of which applicants are aware resulted only in insignificant rate enhancement of the desired reaction. G.P. Royer, 1980, Advances in Catalysis 29:197-227.

During the course of a chemical reaction, the reactants undergo a series of transitions passing through different states until the products are reached. In molecular terms these transitions through intermediate states reflect changes in bond lengths, angles, etc. The transition from reactants to products may be viewed as involving formation of an intermediate which decomposes to produce the products. The overall rate of the reaction can be expressed in terms of the equilibrium constant characterizing the equilibria between the reactants, the intermediate and the products.

Catalysis can be regarded as a stabilization of the intermediate with respect to the state of the reactants. A catalyst is a substance that increases the rate of the reaction and is recovered substantially unchanged chemically at the end of the reaction. Although the catalyst is not consumed, it is generally agreed that the catalyst participates in the reaction.

Despite the commercial importance of catalysis, major limitations are associated with both simple chemical catalysis and enzymatic catalysis. Chemically catalyzed processes often do not produce high yields of desired products. Such processes often result in the production of impurities from side reactions. Furthermore, chemical catalysts are not known for many important chemical reactions. Other limitations include the relatively high cost of catalysts; the requirement for chemical activation; lack of utility under atmospheric conditions or in the presence of small amounts of water; and flammability or explosivity in the presence of atmospheric oxygen. Enzymatic catalysis depends on the existence and discovery of naturally occurring enzymes with the appropriate specificity and catalytic function needed to perform a particular reaction. Enzymes are unknown for many chemical reactions.

The present invention overcomes these limitations by providing a novel approach to catalysis. The invention provides a method for the preparation and use of monoclonal antibodies as convenient, readily obtainable and inexpensive catalysts having a degree of specificity and efficiency of action not previously achievable in the catalytic arts.

SUMMARY OF THE INVENTION

The present invention relates to a method involving monoclonal antibodies for increasing the rate of a chemical reaction involving conversion of at least one reactant to at least one product.

In the practice of this invention, the reactant(s) is (are) contacted with an appropriate monoclonal antibody under conditions suitable for the formation of a complex between the monoclonal antibody and the reactant(s). The complexed reactant(s) is (are) converted to the product(s), and the product(s) released from the complex.

In one embodiment, this invention is useful in increasing the rate of chemical reactions which can also be catalyzed by enzymes such as oxidoreductases, transferases, hydrolases, lyases, isomerases and ligases. In another embodiment, this invention is useful in increasing the rate of chemical reactions for which no catalytic enzymes are known. Such reactions include among others, oxidations, reductions, additions, condensations, eliminations, substitutions, cleavages and rearrangements.

In accordance with this invention the rate of the chemical reaction may be increased by more than a hundred-fold and preferably more than ten thousand-fold.

Conditions suitable for antibody-reactant complex formation are provided by a solution phase or emulsion reaction system including a protic solvent, preferably water, maintained at a pH value between about 6.0 and about 8.0, preferably between about 6.0 and about 7.5, and maintained at a temperature from about 4° C. to about 50° C., preferably between about 20° C. and about 45° C. The ionic strength $\mu = \frac{1}{2}\Sigma c_i z_i^2$, where c is the concentration and z is the charge of an ionic solute. It should be maintained at a value below 2.0 moles/liter, preferably between about 0.1 and 1.5 moles/liter. The method of this invention may be carried out under reduced or elevated pressure, but preferably is practiced at ambient pressure.

A monoclonal antibody appropriate for use in the practice of this invention is characterized by $K>1$, where $K = k_r/k_p$, $k_r$ is the affinity constant of the monoclonal antibody for the reactant and $k_p$ is the affinity constant of the monoclonal antibody for the product. The monoclonal antibody is further characterized by an $r_1 > r_o$, where $r_1$ is the rate of formation of the complex between the antibody and the reactant and where $r_o$ is the rate of the chemical reaction in the absence of monoclonal antibody, by an $r_2 > r_o$, where $r_2$ is the rate of the conversion of the complexed reactant to the complexed product and by an $r_3 > r_o$, where $r_3$ is the rate of release of the product from the complex.

Methods for preparing appropriate monoclonal antibodies are also disclosed. In one embodiment hybridoma cells prepared by modifications of methods well known to those of ordinary skill in the art are screened for the ability to produce appropriate monoclonal antibodies.

In another embodiment anti-idiotype monoclonal antibodies are prepared for known enzyme-substrate systems. The anti-idiotype monoclonal antibodies can be used to increase the rate of conversion of the substrate to the product and are not subject to allosteric control.

DETAILED DESCRIPTION OF THE INVENTION

As indicated above, the present invention provides methods for increasing the rate of a chemical reaction involving conversion of at least one reactant to at least one product. In the practice of this invention, the reactant(s) is (are) contacted with at least one appropriate monoclonal antibody under suitable conditions permitting the formation of a complex between the monoclonal antibody and the reactant(s), conversion of the reactant(s) to the product(s) and release of the product(s) from the complex.

The monoclonal antibodies useful in the present invention are prepared by modification of the technique disclosed closed by Koprowski et al. in U.S. Pat. No. 4,196,265, issued Apr. 1, 1980, which is hereby incorporated by reference. The details of that process are well known to those of ordinary skill in the art. In one embodiment of this invention, a series of monoclonal antibodies directed to the reactant are prepared under suitable conditions. This involves first immunizing BALB/C mice with an appropriate antigen. The antigen may be the desired reactant; the desired reactant bound to a peptide or other carrier molecule; a reaction intermediate or an analog of the reactant, the product or a reaction intermediate. "Analog" as the term is used herein encompasses isomers, homologs or other compounds sufficiently resembling the reactant in terms of chemical structure such that an antibody raised against the analog may participate in an immunological reaction with the reactant but will not necessarily catalyze a reaction of the analog. For example, if the reaction to be catalyzed is the cleavage of o-nitrophenyl- $\beta$-D-galactoside the antigen may be the analog dinitrophenol bound to a carrier, e.g. keyhold limpet hemocyanin, or the antigen may be the reactant o-nitrophenyl-$\beta$-D-galactoside.

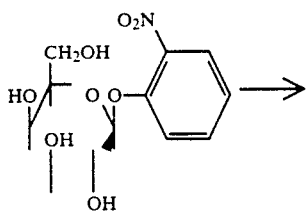

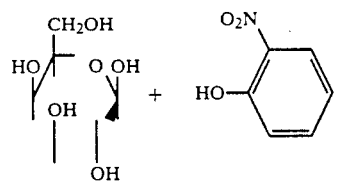

As another example, if the reaction to be catalyzed is the condensation of two molecules of aminolevulinic acid to yield porphobilinogen:

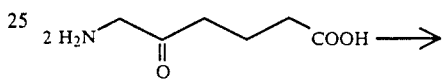

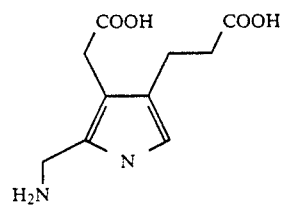

the antigen may be the analog 3-glycyl-4-hydroxy-4-methyl-1,5-heptanedioic acid:

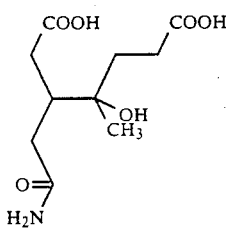

Antibody-producing lymphocyttes are then removed from the spleens of the immunized mice and hybridized with myeloma cells such as SP2/0cells to produce hybridoma cells.

These hybridoma cells are then plated in the wells of microtiter plates. The series of monoclonal antibodies being produced by the hybridoma cells is screened under appropriate conditions to identify monoclonal antibodies which catalyze the desired reaction under appropriate conditions. Screening may be conveniently accomplished by treating a standardized solution of the reactant with an aliquot of medium withdrawn from a microtiter well and measuring the presence of the desired product by conventional instrumental methods. This measurement may be readily conducted, for example by spectophotometric methods or by gas-liquid or high pressure liquid chromatography. By comparison with standardized samples of the desired product or reactant, rates of reaction may be quantified. In this manner, wells containing hybridoma cells producing catalytic monoclonal antibodies are identified. The selected hybridoma cells are then cultured to yield colonies.

These colonies may be further propagated in in vitro or in vivo systems. In the latter case, mice such as syngeneic BALB/C mice are inoculated intraperitoneally with the selected hybridoma cells and produce tumors, generally within two or three weeks. These tumors are accompanied by the production of ascites fluid which contains the desired monoclonal antibodies. The monoclonal antibodies are then separately recovered from the ascites fluid by conventional methods such as ultrafiltration, ultracentrifugation, dialysis and immunoaffinity chromatography.

The monoclonal antibodies of this invention can be characterized by the following equations:

$$K = k_r/k_p \text{ greater than } 1 \qquad (1)$$

$$r_1 > r_o \qquad (2)$$

$$r_2 > r_o \qquad (3)$$

$$r_3 > r_o \qquad (4)$$

In equation (1), K is defined as the ratio of the affinity constant of the monoclonal antibody for the reactant, $k_r$, to the affinity constant of the monoclonal antibody to the product, $k_p$. The equation reflects the fact that the monoclonal antibody has a stronger binding affinity to the reactant than it does to the product. Thus, as a consequence of chemical modification of the reactant to form the product, the binding affinity of the monoclonal antibody for the complexed molecule decreases, and the molecule, the product, is released from the complex, thereby regenerating the free monoclonal antibody catalyst. Preferably K is greater than $10^2$.

Equations (2), (3) and (4) describe the kinetic characteristics of the monoclonal antibodies useful in this invention.

Equation (2) states that $r_1$, defined as the rate of formation of the complex between the antibody and the reactant, must be greater than $r_o$ where $r_o$ is the rate of the chemical reaction in the absence of monoclonal antibody. Equation (3) states that $r_2$, defined as the rate of conversion of the complexed reactant to the complexed product, must be greater than $r_o$. Equation (4) states that $r_3$, defined as the rate of release of the product from the complex, must be greater than $r_o$. Those skilled in the art will recognize that the rates $r_o$, $r_1$, $r_2$ and $r_3$ may conveniently be determined directly or indirectly by known methods.

As a result of these characteristics, the monoclonal antibodies of this invention can effect a rate acceleration in chemical reactions preferably by more than a factor of $10^2$ and even more preferably by more than a factor of $10^4$.

In accordance with this invention the separately recovered monoclonal antibodies are contacted with the reactant under suitable conditions permitting the formation of a complex between the monoclonal antibody and the reactant. Those of ordinary skill in the art will appreciate that the conditions suitable for complex formation may vary depending on the particular reactant and monoclonal antibody under consideration. Accordingly, the methods of this invention may be practiced under a variety of reaction conditions, as long as the monoclonal antibodies are not prevented from complexing with the reactant(s) or otherwise rendered inactive. More specifically, suitable conditions for complex formation encompass solution phase and emulsion reaction systems including a protic solvent, preferably water, maintained at a pH value between about 6.0 and about 8.0, preferably between about 6.0 and about 7.5 and at a temperature from about 4° C. to about 50° C., preferably from about 20° C. to about 45° C. The ionic strength, $\mu = \frac{1}{2}\Sigma c_i z_i^2$, where c is the concentration and z is the electronic charge of an ionic solute, should be maintained at a value below about 2.0 moles/liter, preferably between 0.1 and 1.5 moles/liter. The method of this invention may be carried out at reduced or elevated pressure, but preferably is practiced at ambient pressure. In addition to solution phase and emulsion reaction systems, suitable conditions also include the use of support materials to which the monoclonal antibody is attached. Such support materials are well-known to those of ordinary skill in the art as are methods for attaching monoclonal antibodies to them.

The method of this invention is widely useful to increase the rate of any chemical reaction. This method is applicable, for example, to chemical reactions involving the conversion of one reactant to one product. Such reactions include the conversion of an α-keto acid to an α-amino acid, and can be illustrated by the conversion of indole pyruvic acid to L-tryptophan. Another example is provided by the conversion of a cyclic polynucleotide to a linear polynucleotide, the term "polynucleotide" being used herein to include both poly- and oligonucleotides.

The method of this invention is also applicable to chemical reactions of more complex stoichiometry. The rate of reactions involving the conversion of two reactants to one product, for instance can also be increased in accordance with this invention. An example of such a reaction is the conversion of two molecules of aminolevulinic acid into one molecule of porphobilinogen.

The method is also useful for reactions involving the conversion of one reactant into two products. Such reactions may be illustrated by the conversion of a β-D-galoctoside into D-galactose and a second product, as well as by the cleavage of a polynucleotide, polypeptide or polysaccharide into two fragments derived respectively therefrom. As used herein the terms "polypeptide" and "polysaccharide" include poly- and oligopeptides and poly- and oligosaccharides, respectively.

The method has further utility in increasing the rate of chemical reactions involving the conversion of one reactant into multiple products. Such reactions include among others, the conversion of polynucleotides, polypeptides and polysaccharides into fragments derived respectively therefrom.

In another embodiment of this invention, a reactant is contacted with more than one monoclonal antibody each of which is directed to a different determinant on the reactant. Thus, where the reactant is a polynucleotide and the monoclonal antibodies are directed to different nucleotide sequences within the polynucleotide, specific polynucleotide fragments may be cleaved from the reactant.

The method is also useful in increasing the rate of reactions involving the conversion of two reactants into two products. Such reactions include the exchange of functional groups between one reactant and a second reactant to yield two new products, e.g. transesterification.

The preceding enumeration of stoichiometries is not meant to be exclusive; rather it is intended to indicate the wide scope of utility of the present invention and indeed that this method is not limited by the stoichiometry of the reaction under consideration.

As is evident also by the preceding discussion and illustrative examples, the method of this invention is useful over the wide variety of chemical reactions including oxidations, reductions, additions, condensations, eliminations, substitutions, cleavages and rearrangements among others.

These examples also illustrate the high degree of catalytic specificity characteristic of this invention. In the practice of this invention, for instance, monoclonal antibodies may be prepared which interact with a polynucleotide only at a specific nucleotide sequence or with a peptide only at a specific amino acid sequence.

The method of this invention may be used to increase the rate of reactions which may also be catalyzed by an enzyme. For example, the enzyme may be an oxidoreductase, such as alcohol dehydrogenase, glucose oxidase, xanthine oxidase, dihydrouracil dehydrogenase or L-amino acid oxidase; a transferase such as guanidinoacetate methyl transferase, serine hydroxymethyl transferase or aspartate aminotransferase; a hydrolase such as acetylcholinesterase, glucose-6-phosphatase or a phosphodiesterase; a lyase such as pyruvate decarboxylase, aldolase or histidine ammonia-lyase; an isomerase such as ribulose phosphate epimerase or a ligase such as tyrosyltRNA synthase or acetyl CoA carboxylase.

As indicated previously, this method may be used to increase the rate of conversion of two molecules of aminolevulinic acid to one molecule of porphobilinogen, a reaction catalyzed in nature by the enzyme aminolevulinic acid dehydratase; to increase the rate of conversion of a cyclic polynucleotide to a linear polynucleotide or of a linear polynucleotide to two or more fragments thereof, reactions involving cleavage of a specific phosphodiester bond in the polynucleotide catalyzed in nature by phosphodiesterase (restriction) enzymes; to increase the rate of conversion of an $\alpha$-keto acid such as indole pyruvic acid to an $\alpha$-amino acid such as L-tryptophan, a reaction involving transfer of an amino group from a reactant to a product catalyzed in nature by a transaminase enzyme; and to increase the rate of conversion of a $\beta$-D-galactoside to D-galactose and second product, a reaction involving cleavage of a $\beta$-Dgalactoside linkage catalyzed in nature by $\beta$-D-galactosidase.

In another embodiment of this invention monoclonal antibodies directed to an antigen which is a known substrate for an enzyme are prepared and used to increase the rate of conversion of the substrate to the product. This method is useful for example in increasing the rate of conversion of o-nitrophenyl-$\beta$-D-galactoside, a known substrate for the enzyme $\beta$-D-galactosidase, to o-nitrophenol and D-galactose. In this method, a series of monoclonal antibodies to the enzyme are prepared by inoculating BALB/C mice with the enzyme and proceeding according to the general technique described above. The series of antibodies so produced is screened under suitable conditions to identify a first monoclonal antibody which binds to the active site of the enzyme. Such a monoclonal antibody may be identified by screening for antibodies which under appropriate conditions inhibit binding of the antigen (substrate) to the enzyme. This screening process may be conveniently carried out by conventional methods of measuring enzyme binding activity, e.g. radioimmunoassay (RIA). This first monoclonal antibody so identified is separately recovered according to the general technique and is used to inoculate fresh BALB/C mice. By following the general technique a series of monoclonal antibodies to the first monoclonal antibody is produced. The antibodies so produced are termed "anti-idiotype" monoclonal antibodies. The series of anti-idiotype monoclonal antibodies is then screened according to the general method to identify anti-idiotype monoclonal antibodies which bind the antigen (substrate) under suitable conditions and convert it to the product. By "suitable conditions," are meant conditions within the parameters described above for antibody-reactant complex formation. An antiidiotype monoclonal antibody so produced and separately recovered may be used in accordance with this invention to increase the rate of conversion of substrate to product.

Using such a monoclonal antibody in place of the enzyme in this embodiment of the invention is especially advantageous where the enzyme is allosteric. Allosteric enzymes are enzymes which are stimulated or inhibited by a modulator molecule which may be the substrate, the product or some other molecule. As a result the kinetic behavior of allosteric enzymes is greatly altered by variations in the concentration of the modulator(s). A relatively simple example of allosteric behavior may be illustrated by an enzyme which is subject to feedback inhibition. In such a case, the catalytic efficiency of the enzyme decreases as the concentration of an immediate or subsequent product increases. Use of such enzymes in many applications is thus limited and requires continuous removal of product. In accordance with this invention, use of the appropriate anti-idiotype monoclonal antibody which is not subject to allosteric control in place of the enzyme can thus overcome the problems and limitations of allosterism.

It is also contemplated that the method of this invention can be used to increase the rate of reactions which can also be catalyzed by non-proteinaceous organic molecules, hereinafter termed cofactors, such as pyridoxal phosphate, nicotinamide adenine dinucleotide, nicotinamide adenine dinucleotide phosphate, flavin adenine dinucleotide, adenosine triphosphate, thiamine pyrosphospohate, flavin mononucleotide, biotin, tetrahydrofolic acid, coenzyme B12 and coenzyme A. Reactions which can be catalyzed by pyridoxal phosphate, for instance, include the inter-conversion of $\alpha$-keto acids and $\alpha$-amino acids. This and other reactions catalyzed by cofactors alone are relatively slow and non-selective. To overcome the problems encountered in using the cofactor alone, a monoclonal antibody may be prepared in accordance with this invention that combines the relatively inefficient catalytic capabilities of a cofactor alone with the highly specific and efficient advantages of the monoclonal antibody. To prepare such a monoclonal antibody, mice are inoculated with the cofactor bound to the reactant or to an analog of the reactant or product, and the general technique of Koprowski described above is followed. A series of hybridoma cells is then prepared according to the general method and screened for the production of monoclonal antibodies which can complex with free cofactor and reactant, increase the rate of the chemical reaction and release the product. Such a monoclonal antibody directed against indole pyruvic acid-pyridoxamine phosphate imine, for example, selectively increases the rate of conversion of indole pyruvic acid to the amino acid tryptophan. In the practice of this embodiment of the invention the appropriate cofactor is added to the reaction mixture preferably in an amount at least equimolar to that of the monoclonal antibody.

The following examples are set forth to illustrate specific embodiments of the invention.

MATERIALS AND METHODS

In the Examples below the chemical and biological reagents were obtained from commercial sources as follows: o-nitrophenyl-$\alpha$-D-galactosidase and buffers were obtained from Sigma Chemical Co., Saint Louis, Miss.; dinitrophenol (DNP) and dinitrobenzene sulfonate were obtained from Eastman Kodak Co., Rochester, N.Y.; goat anti-mouse immunoglobulin labeled with horseradish peroxide and 2,2'-azino-di(3-ethylbenzthiazoline sulfonic acid) (ABTS) were obtained from KPL Laboratories, Inc., Gaithersburg, Md.; microtiter plates (Immulon II ®) were obtained from Dynatech, Alexandria, Va.; kanomycin was obtained from GIBCO Laboratories, Grand Island, N.Y.; fetal calf-serum and keyhole limpet hemocyanin and other proteins can be obtained from Calbiochem-Behring, San Diego, Calif.; cell growth media and supplements can be obtained from M.A. Bioproducts, Walkersville, Md.; Sp20 myeloma cells (ATCC CRL 1581) were obtained from the American Type Culture Collection, Rockville, Md.; other reagents, e.g. o-nitrophenyl-$\beta$-D-galactoside, 5-aminolevulinic acid, hydrogen peroxide, phenol, magnesism sulfate, sodium bicarbonate, indole-3-pyruvic acid, pyridoxal 5-phosphate molecular sieves and morpho CDI can be obtained from Aldrich Chemical Co., Saint Louis, Mo. BALB/C mice were obtained from the National Cancer Institute, Frederick Research Facility, Fredrick, Md. Adjuvants were obtained from Sigma. Mouse mammary tumor virus RNA may be extracted by conventional methods from a commercially available mouse mammary tumor virus, e.g. MTV ATCC VR-731 (American Type Culture Collection). The analog 3-glycyl-4- hydroxy-4-methyl-1,5-heptanedioic acid may be prepared by conventional synthetic methods, e.g. by base catalyzed condensation suitably protected molecules of aminolevulinic acid and levulinic acid (Aldrich) followed by deprotection and HPLC purification.

EXAMPLE 1

Immunization of Mice with
o-Nitrophenyl-$\beta$-D-Galactoside

One group of female BALB/C mice (Group 1 in Table 1) at 7 weeks of age were inoculated intravenously with 10 mg. of o-nitrophenyl-$\beta$-D-galactoside (ONPG) and intraperitoneally with 12 mg. of ONPG on day 0. The ONPG was dissolved in 0.1 M phospate buffer at pH 7.3 at a concentration of 25 mg/ml and warmed to 37° C. On day 33 the mice were inoculated intraperitoneally with 12.5 mg. of ONPG in incomplete Freund's adjuvant. The ONPG phospate buffer solution was mixed with an equal volume of incomplete Freund's adjuvant and emulsified prior to inoculation. A blood sample was obtained from each mouse on day 54. The serum was separated from the blood sample by centrifugation and stored at 4° C.

EXAMPLE 2

Immunization of Mice with DinitrophenolKeyhole Limpet Hemocyanin Conjugate

Mice inoculated as in Example 1 were inoculated intraperitoneally on day 91 with dinitrophenol (DNP) coupled to keyhole limpet hemocyanin (KLH) and emulsified in incomplete Freund's adjuvant. The inoculum contained 10 mg. of protein as determined by the method of Bradford, 1976, Anal. Biochem. 72:248. The dinitrophenol was coupled to KLH by the method of Little and Eisen, 1967, Meth. Immunol. Immunochem. 1:12. The DNP-KLH inoculation was repeated on day 101. The inoculum was prepared as described for the inoculum used on day 91. A blood sample was obtained from each mouse on day 105 and the serum separated by centrifugation and stored at 4° C.

EXAMPLE 3

Immunization of Mice with
o-Nitrophenyl-$\beta$-D-Galactoside

BALB/C mice (Group 2 in Table 1) were inoculated intraperitoneally with 50 mg. or 100mg. of ONPG emulsified in complete Freund's adjuvant on day 0, intravenously, with 10 mg. of ONPG in 0.1 M phosphate buffer (pH 7.3) on day 30, and intraperitoneally with 12.5 mg. of ONPG in incomplete Freund's adjuvant (25 mg/ml) on day 63. The mice were bled 9 days later, serum was separated by centrifugation and stored at 4° C.

EXAMPLE 4

Immunization of Mice with DinitrophenolKeyhole Limpet Hemocyanin Conjugate

Mice inoculated as in Example 3 were then inoculated, intraperitoneally, with 10 mg. of DNP-KLH emulsified in incomplete Freund's adjuvant on days 121 and 131, and bled on day 135. Serum was separated by centrifugation and stored at 4° C.

EXAMPLE 5

Evaluation of Mouse Sera

A. Preparation of Microtiter Plate Wells

Fifty (50) microliters of a solution containing ONPG in carbonate buffer (1 mg/ml) was added to each well of a polystyrene microtiter plate. After 18 hr. at 4° C. the solution was removed and the wells washed 4 times with phosphate buffered saline containing 0.05% Tween-20 (PBSTween). The ONPG-coated wells were then blocked by incubating the wells with PBS-tween containing 1% bovine serum albumin (BSA) for 120 min. at 37°.

B. ONPG-Binding Assay

Sera collected in Examples 1 and 3 and serum from mice which had not been immunized were diluted to various degrees with PBS-tween containing 1% BSA. Aliquots of the solution so prepared were added to ONPG-coated wells prepared as described above and incubated at 37° C. for 120 min. The solutions were then removed and the wells washed 4 times with PBS-Tween. The presence of serum antibodies binding to ONPG was detected by the method of Engvall and Perlman, 1971. Immunochem. 8:871 using an anti-mouse goat immunoglobulin conjugated with horseradish peroxidase. After unbound anti-mouse antibody was removed from the wells by washing, 2,2'-azino-di (3- ethylbenzthiazoline sulphonic acid) (ABTS) and hydrogen peroxide were added to each well and left in contact with the well for 15 to 20 min. Colored product was detected in the wells that were contacted with 1:10 to 1:320 dilutions of serum from mice immunized with ONPG. Of the sera collected in Example 3, that obtained from mice initially inoculated with 100 mg. of ONPG had a titer greater than 1:320, which was at least two-fold greater than the titer of serum obtained from mice initially inoculated with 50 mg. of ONPG. Serum from mice not immunized with ONPG did not produce colored product in this assay. These results demonstrated that serum from mice immunized with DNPG contained antibodies that bound ONPG.

C. Assay for Activity in Catalyzinq the Cleavage of ONPG

The catalytic activity of antibodies which react with ONPG was determined in the following way. Fifty (50) microliters of diluted mouse serum obtained in Examples 1 and 3 as described above was contacted for 18 hours at 23° C. with 50 microliters of ONPG in PBS-Tween buffer containing 1% BSA. Similarly, 50 ng. of the enzyme β-D-galactosidase in 50 microliters of PBS-Tween-BSA buffer was contacted with the ONPG solution. Catalytic activity resulting in the formation of β-D-galactose and o-nitrophenol, which has a yellow color, was not detected with any of the serum samples. As expected the enzyme β-D-galactosidase had catalytic activity.

Serum collected in Examples 2 and 4 from mice which had received additional inoculations with DNP coupled to KLH was then assayed. The serum was tested for the presence of antibodies that bind ONPG by the method described above. It was shown that serum from the immunized mice contained anti-OPNG antibodies. Serum at a dilution of 1:5,120 yielded a positive reaction for the presence of anti-ONPG antibodies. This demonstrated that additional immunizations with an analog coupled to KLH had resulted in an increased concentration of anti-ONPG antibodies in the serum. No reactions were seen using serum from mice that had not been immunized.

The catalytic activity of the serum antibodies in the serum collected in Examples 2 and 4 was tested as described above.

The results are shown in Table 1 and demonstrate that catalytic activity was detected in serum samples from the immunized mice.

TABLE 1

| Catalytic Activity of Mouse Sera and β-D-Galactosidase | | | |
|---|---|---|---|
| | Absorbance at 405 nm[1] | | |
| Serum Dilutions | 10 min. | 18 hrs. | ΔAbsorbance[2] |
| Group 1[3] ONPG antisera | | | |
| 1:10 | .019 | .023 | .004 |
| 1:20 | .005 | .003 | .000 |
| 1:40 | .008 | .010 | .002 |
| Group 2[4] ONPG antisera | | | |
| 1:10 | .006 | .031 | .025 |
| 1:20 | .004 | .042 | .038 |
| 1:40 | .006 | .009 | .003 |
| Normal mouse sera | | | |
| 1:10 | .003 | .009 | .006 |
| 1:20 | .000 | .000 | .000 |
| 1:40 | .005 | .007 | .002 |
| β-D-galactosidase | | | |
| 50 ng | .229 | .362 | .133 |
| 5 ng | .029 | .496 | .467 |
| 0.5 ng | .000 | .112 | .112 |

[1] Corrected for absorbance of serum.
[2] Difference in value, at 10 min. and 18 hrs.
[3] Sera obtained in Example 2
[4] Sera obtained in Example 4

EXAMPLE 6

Preparation of Spleen Cells for Fusion (Hybridization) By Immunization with o-nitrophenyl-β-D-galactoside Antibody-producing mice immunized as in Example 4 and assayed as in Example 5 are sacrificed and their spleens removed. The spleens of ten (10) mice are gently teased and passed through a fine nylon screen to yield a lymphocyte (spleen cell) suspension. The suspension is washed three (3) times in serum-free RPMI-1640.

EXAMPLE 7

Preparation of Myeloma Cells for Fusion (Hybridization)

Myeloma cells derived from the SP2/0 line are grown in HB101 medium supplemented with 2% fetal bovine serum, penicillin and streptomycin (complete HB101). SP2/0 cells are subcultured daily for three days before use in cell fusions and are seeded at densities not exceeding $10^5$ cells/ml. The SP2/0 cells are washed once in RPMI-1640 before fusion.

EXAMPLE 8

Preparation of Hybridoma Cells

A suspension of lymphocytes prepared as in Example 6 is mixed in a 4:1 ratio with a suspension of SP2/0 myeloma cells prepared according to Example 7.

The cells are pelleted and a polyethylene glycol (PEG) 1450 (Eastman-Kodak, Rochester, NY) solution (containing 50% PEG wt/vol in RPMI-1640) is then added dropwise to the cell pellets at a ratio of 1 ml of PEG to $1.6 \times 10^5$ lymphocytes. After cell fusion with the PEG solution, the cell suspension is centrifuged at 200xg for 5 min., the supernatant is removed and the cells are gently suspended in complete HB101 at a final concentration of $10^7$ cells per ml. This final cell suspension is then dispensed in 100 μl volumes in wells of a 96-well microtiter plate and cultured at 37° C. After 24 hours, 100 μl of HAT medium (complete HB101 supplemented with $1 \times 10^{-4}$ M hypoxanthine, $4.0 \times 10^{-7}$ M aminopterin, and $1.6 \times 10^{31}$ =M thymidine) is then added to each well. Cells are fed every 2 to 3 days by aspirating approximately 100 μl of medium from each well and adding 100 μl of fresh HAT medium.

Extensive death of the parental myeloma cells and lymphocytes is observed during week one of culture in HAT medium.

Ten to fifteen days after incubation, cell growth in the HAT medium indicative of successful hybridization is observed.

EXAMPLE 9

Screening the Hybridoma Cells Producing Catalytic MonoScreening clonal Antibodies Microtiter wells containing hybridoma cells prepared according to Example 8 which produce antibodies capable of catalyzing the cleavage of 0-nitrophenyl-β-D-galactoside into o-nitrophenol and D-galoctose are assayed as follows: a second 96-well microtiter plate (the assay plate) is prepared containing a 0.05 M solution of o-nitrophenyl-β-D-galoctoside in each well and maintained at 37° C. A 100 βl aliquot of the contents of each hybridoma-containing well of the first plate (hybridoma plate) is withdrawn and transfered to a corresponding well of the assay plate. Preferably the presence of onitrophenol is measured spectrophotometrically. Alternatively, five (5) minutes after each transfer a 50 μ l aliquot of the assay plate well is analyzed by HPLC for the presence of one or both of the products. Each assayplate well found to contain o-nitrophenol and D-galactose is identified and the corresponding hybridoma plate well is marked.

EXAMPLE 10

Culturing Hybridoma Cells

A portion of each catalytic hybridoma cell suspension identified in Example 9 is seeded in each well of a new microtiter plate. The plating efficiency of the hybrid cells is 50% (i.e., 50% of the seeded cells multiply to form colonies). With this procedure 80-100% of the wells yield colonies of hybrid cells within two (2) weeks. The hybridoma cells are again tested for catalytic antibody production by the method described in Example 9. Hybridoma cells which continue to produce catalytic antibodies are again cloned using thymocyte feeder cells, but at densities of one hybrid cell per three wells. The procedure is repeated whenever less than 90% of the clones from a specific set are making antibodies.

EXAMPLE 11

Catalytic Monoclonal Antibodies In Vivo

Intraperitoneal inoculation of $10^6$ hybrid cells selected according to Example 9 into syngeneic BALB/C mice induces palpable tumors in more than 90% of the inoculated mice within 2 to 3 weeks. These tumors are accompanied by the production of ascites fluids (0.5 to 3.0 ml per mouse). The immunoglobulin concentration in ascites fluids and sera of hybridoma-bearing mice is determined by a radial immunodiffusion assay. The concentrations of monoclonal antibodies in the serum and ascites fluid of an individual mouse are roughly equivalent, each containing 5 to 50 mg of antibody per ml. The monoclonal antibody capable of catalyzing the cleavage of o-nitrophenyl-β-D-galactoside is then harvested from the serum or ascites fluid by conventional methods such as gel filtration or ultrafiltration.

EXAMPLE 12

Use of a Monoclonal Antibody to Catalyze the Cleavage of o-Nitrophenyl-β-D-Galactoside To a solution containing 30.12 g (100 mmol) o-nitrophenyl-β-D-galoctoside in 1000 ml distilled water buffered at pH 6.8 with 0.5 M phosphate buffer and maintained at 37° C. is added 10 mg of monoclonal antibodies prepared according to Example 6. The reaction mixture is gently agitated for 2.0 hours. The monoclonal antibodies are then recovered from the reaction mixture by ultrafiltration. The filtrate is then cooled to 10° C. and treated with 9.2 g (110 mmol) sodium bicarbonate. The D-galactose is recovered by extracting the filtrate with three 100 ml portions of diethyl ether. The ether portions are combined, washed once with 1.0 N sodium bicarbonate, dried over magnesium sulfate, filtered and concentrated under reduced pressure to yield D-galactose. The aqueous portion is then combined with the sodium bicarbonate wash and acidified to pH 3 by the addition of 5 N hydrochloric acid. The acidified aqueous portion is then extracted three times with ether. The etheral extracts are combined, dried over magnesium sulfate, filtered and concentrated at reduced pressure to yield o-nitrophenol. The o-nitrophenol and D-galactose may be further purified by HPLC or by recrystallization.

EXAMPLE 13

Preparation of Catalytic Monoclonal Antibodies for Porphobilinogen (PBG) Production Spleen cells for hybridization are prepared according to the method of Example 6, except that the BALB/C mice are immunized with 3-glycyl-4-hydroxy-4-methyl-1,5-heptanedioic acid. Myeloma cells are prepared according to Example 7. The spleen cells and the myeloma cells are then fused to yield hybridoma cells according to the method of Example 8. The hybridoma cells are then screened by a modification of the method of Example 9 in which the assay substrate is aminolevulinic acid (0.05 M) and the assay tests for the appearance of an HPLC-peak corresponding to PBG. The hybridoma cells so identified are cultured according to the method of Example 10 and are obtained from mice according to the method of Example 11

EXAMPLE 14

Use of Monoclonal Antibodies to Catalyze the Production of PBG

To a solution containing 13.1 g (100 mmol) aminolevulinic acid in 1000 ml of distilled water buffered at pH 6.8 with 0.5 M phosphate buffer and maintained at 37° C. is added 30 mg of the monoclonal antibodies prepared according to Example 13. The reaction mixture is gently agitated for 2.0 hours. The monoclonal antibodies are then recovered from the reaction mixture by ultrafiltration. The reaction mixture is lyophilized, and the residue is chromatographed to yield purified PBG.

EXAMPLE 15

Preparation of Catalytic Monoclonal Antibodies for L-Tryptophan Production

A Schiff base is prepared by mixing 2.03 g (10 mmol) indole-3-pyruvic acid, 2.65 g (10 mmol) pyridoxamine phosphate and 3 g of dry 4Å molecular sieves in dry methanol under a nitrogen atmosphere. The reaction mixture is gently agitated overnight, filtered and concentrated under reduced pressure to yield the Schiff base. Spleen cells are prepared by the method of Example 6 except that the BALB/C mice are immunized with the Schiff base. The spleen cells so obtained are fused according to the method of Example 8 with myeloma cells prepared according to Example 7. The hybridoma cells are then screened by a modification of the method of Example 9 in which the substrate is a mixture of indole-3-pyruvic acid (0.05 M) and pyridoxamine-5-phosphate (0.05 M) and the assay tests for the appearance of an HPLC peak corresponding to L-tryptophan. The hybridoma cells so identified are cultured according to the method of Example 10 and are obtained from mice by the method of Example 11.

EXAMPLE 16

Use of Monoclonal Antibodies to Catalyze the Production of L-Tryptophan

To a solution containing 20.3 g (100 mmol) of indole-3-pyruvic acid and 26.5 g (100 mmol) of pyridoxamine-5-phosphate in 1000 ml of distilled water buffered at pH 6.5 with 0.5 M phosphate buffer and maintained at 37° C. is added 50 mg of the monoclonal antibodies prepared according to Example 15. The reaction mixture is gently agitated for 2 hours. The monoclonal antibodies are then recovered by ultrafiltration. Dialysis of the reaction mixture followed by lyophilization yields the product L-tryptophan.

EXAMPLE 17

Preparation of Catalytic Monoclonal Antibodies Capable of Cleaving RNA at a Specific Nucleotide Sequence (A) Preparation of the Antigen To a solution of bovine serum albumin (BSA) (50 mg) dissolved in cold water (8 ml) and titrated to pH 6.5 with 0.1 N sodium hydroxide, is added 1-cyclohexyl-3-(2-morpholinoethyl) carbodiimide metho-p-toluenesulfonate (morpho CDI) followed immediately by mouse mammary tumor virus 35S RNA (50 mg). The reaction mixture is allowed to warm to room temperature and is stored for 18 hours with periodic gentle agitation. The reaction mixture is then dialyzed against four changes of 0.05 M ammonium bicarbonate followed by four changes of water. The RNA-protein (BSA) conjugate is then lyophilized and weighed into vials for storage under nitrogen at −77° C. Alternatively, keyhole limpet hemocyanin (KLH), ovalbumin (OA) and rabbit serum albumin (RA) may be used in place of BSA. All of these proteins are obtainable from Calbiochem.

(B) Preparation of the Monoclonal Antibodies

Spleen cells for hybridization are prepared according to the method of Example 6, except that the BALB/C mice are immunized with the BSA-bound 35S RNA prepared in (A) above. Myeloma cells are prepared according to Example 7. The spleen cells and the myeloma cells are then fused to yield hybridoma cells according to the method of Example 8.

The hybridoma cells so obtained are screened by incubating aliquots of the microtiter well contents with 35S RNA in 0.5 M phosphate buffer (pH 6.1) containing 0.9% NaCl at 37° C. for varying lengths of time. The RNA is then purified by phenol extraction. The number of fragments generated by antibody cleavage is determined by 2-dimensional polyacrylamide gel electrophoresis and the nucleotide sequence at each cleavage site is resolved. Both determinations are made according to the methods described by Schwartz et al. in Cell 32: 853–869 (1983). By comparing the fragments obtained from RNA cleavage induced by the contents of each microtiter well with Eco Rl-induced fragments, hybridoma cells are selected which produce monoclonal antibodies capable of catalyzing RNA cleavage only at Eco Rl cleavage sites. The hybridoma cells so identified are cultured according to the method of Example 10 and are obtained from mice by the method of Example 11.

EXAMPLE 18

Use of Monoclonal Antibodies to Catalyze RNA Cleavaqe at Eco Rl Sites

Mouse mammary tumor virus 35S RNA (50 mg) is added to 100 ml of distilled water buffered at pH 6.1 with 0.5 M phosphate buffer containing 0.9% NaCl and maintained at 37° C. Monoclonal antibodies (5 mg) prepared according to Example 17 are added to the reaction mixture which is then incubated for 30 minutes with gentle agitation. The RNA is then purified by phenol extraction and the fragments purified by polyacrylamide gel electropherosis.

EXAMPLE 19

Anti-idiotype Monoclonal Antibodies to β-D-galactosidase (A) Preparation of Monoclonal Antibodies to the Enzyme Active Site Spleen cells for hybridization are prepared according to the method of Example 6, except that the BALB/C mice are immunized with the enzyme β-D-galactosidase. Myeloma cells are prepared according to Example 7. The spleen cells and the myeloma cells are then fused to yield hybridoma cells according to the method of Example 8. The hybridoma cells thus obtained are screened for production of monoclonal antibodies which bind to the active site of the enzyme. Screening is conveniently conducted by RIA assay of the competitive inhibition of the microtiter well contents against β-D-galactosidase and radiolabeled o-nitrophenyl-β-D-galactoside. Hybridoma cells so selected are then cultured according to the method of Example 10 and obtained in larger quantity from mice according to the method of Example 11.

(B) Preparation of the Anti-idiotype Monoclonal Antibody

Spleen cells for hybridization are prepared according to the method of Example 6, except that the BALB/C mice are immunized with the monoclonal antibodies prepared and selected according to (A) above. Myeloma cells are again prepared according to Example 7. The spleen cells and the myeloma cells are fused to yield hybridoma cells according to the method of Example 8. The hybridoma cells thus obtained are first screened according to the method of Example 9. Hybridoma cells selected on the basis of the preliminary screening are then screened for allosterism. This is accomplished by measuring the presence of one of products according to Example 9, but at periodic time intervals. From the data so obtained, a reaction rate may be calculated. By repeating the assay in the presence of varying amounts of the reactant and again with varying amounts of the product not being measured, changes in the kinetic behavior of the antibody can be detected. In this manner, anti-idiotype monoclonal antibodies exhibiting allosteric control may be eliminated. The hybridoma cells producing non-allosteric anti-idiotype monoclonal antibodies are cultured according to the method of Example 10 and obtained by propagation in mice according to the method of Example 11.

(C) Use of Anti-idiote Monoclonal Antibodies

The anti-idiotype monoclonal antibodies obtained in (B) may be used according to the method of Example 12.

What is claimed is:

1. A method for producing a catalytic monoclonal antibody which is capable of catalytically increasing the rate of a chemical reaction wherein at least one reactant is converted to at least one product comprising the steps of:
   (a) generating a plurality of monoclonal antibodies to an antigen selected from the group consisting of:
      (i) the reactant;
      (ii) the reactant bound to a peptide or other carrier molecule;
      (iii) a reaction intermediate;
      (iv) an analog of the reactant;
      (v) an analog of the product in which the monoclonal antibody so generated is capable of binding to the reactant or a reaction intermediate; and
      (vi) an analog of a reaction intermediate; and
   (b) screening said plurality of monoclonal antibodies to identify a monoclonal antibody which catalyzes the reaction.

2. A method as recited in claim 1 wherein said antigen is bound to a carrier molecule.

3. A method as recited in claim 1 wherein said analog is a compound which structurally resembles said reactant, reaction intermediate or reaction product to such a degree that an antibody raised against said analog participates in an immunological reaction but does not necessarily catalyze a reaction of said analog.

4. A method as recited in claim 3 wherein said analog is an isomer or homolog of said reactant, reaction intermediate or product.

5. A method as recited in claim 1 wherein said antigen is an analog of the reactant.

6. A method as recited in claim 1 wherein said reaction is one which is also capable of being catalyzed by a cofactor or by an enzyme and a cofactor or enzyme is present in said reaction.

7. A method as recited in claim 1 wherein the monoclonal antibody identified in step (b) is produced in quantity by culturing a plurality of hybridoma cells each of which produces said monoclonal antibody.

8. A method for producing catalytic monoclonal antibodies which are capable of catalytically increasing the rate of a chemical reaction wherein at least one reactant is converted to at least one product comprising the steps of:
   (a) generating a plurality of monoclonal antibodies to an antigen selected from the group consisting of:
      (i) the reactant;
      (ii) the reactant bound to a peptide or other carrier molecule;
      (iii) a reaction intermediate;
      (iv) an analog of the reactant;
      (v) an analog of the product in which the monoclonal antibody so generated is capable of binding to the reactant or a reaction intermediate; and
      (vi) an analog of a reaction intermediate;
   (b) screening said plurality of monoclonal antibodies to identify a monoclonal antibody which catalyzes the reaction; and
   (c) producing a quantity of the monoclonal antibody identified in step (b).

9. A method for producing a catalytic monoclonal antibody which is capable of catalytically increasing the rate of a chemical reaction wherein at least one reactant is converted to at least one product comprising the steps of:
   (a) immunizing an animal with an antigen selected from the group consisting of
      (i) the reactant,
      (ii) the reactant bound to a peptide or other carrier molecule,
      (iii) a reaction intermediate,
      (iv) an analog of the reactant,
      (v) an analog of the product in which the monoclonal antibody so generated is capable of binding to the reactant or a reaction intermediate, and
      (vi) an analog of a reaction intermediate, thereby generating antibody-producing lymphocytes in said animal;
   (b) removing said antibody-producing lymphocytes from said animal;
   (c) fusing said antibody-producing lymphocytes with myeloma cells and thereby producing a plurality of hybridoma cells each producing monoclonal antibodies; and
   (d) screening said plurality of monoclonal antibodies to identify a monoclonal antibody which catalyzes the reaction.

10. A method as recited in claim 9 wherein said analog is a compound which structurally resembles said reactant, said product or said reaction intermediate to such a degree that an antibody raised against said analog participates in an immunological reaction but does not necessarily catalyze a reaction of said analog.

11. A method as claimed in claim 9 wherein said antigen is bound to a carrier molecule.

12. A method as claimed in claim 10 wherein said analog is a isomer or homolog of said reactant, product or reaction intermediate.

13. A method for producing catalytic monoclonal antibodies which are capable of catalytically increasing the rate of a chemical reaction which is known to be catalyzed by an enzyme and wherein at least one reactant is converted to at least one product comprising the steps of:
   (a) generating a plurality of monoclonal antibodies to said enzyme;
   (b) screening said plurality of monoclonal antibodies to identify a first monoclonal antibody which inhibits binding of the reactant to the enzyme;
   (c) recovering the said first monoclonal antibody;
   (d) generating a plurality of anti-idiotype monoclonal antibodies to the said first antibody recovered in step (c);
   (e) screening said plurality of anti-idiotype monoclonal antibodies generated in step (d) to identify a second monoclonal antibody which binds the reactant and catalytically increases the rate of the reaction; and
   (f) producing a quantity of the monoclonal antibody identified in step (e) by culturing a plurality of hybridima cells, each of the which produces said monoclonal antibody.

* * * * *